United States Patent
Lowe et al.

(10) Patent No.: US 8,403,857 B2
(45) Date of Patent: Mar. 26, 2013

(54) FLEXIBLE OESOPHAGEAL DOPPLER MONITORING PROBE

(75) Inventors: Graham Desmond Lowe, Hayling Island (GB); William Roger Skeens, Southbourne (GB)

(73) Assignee: Deltex Medical Limited (GB)

( * ) Notice: Subject to any disclaimer, the term of this patent is extended or adjusted under 35 U.S.C. 154(b) by 1000 days.

(21) Appl. No.: 12/116,824

(22) Filed: May 7, 2008

(65) Prior Publication Data
US 2009/0281427 A1    Nov. 12, 2009

(51) Int. Cl.
*A61B 8/06* (2006.01)
(52) U.S. Cl. .................................................. 600/465
(58) Field of Classification Search .................. None
See application file for complete search history.

(56) References Cited

U.S. PATENT DOCUMENTS

| | | | |
|---|---|---|---|
| 4,796,634 A * | 1/1989 | Huntsman et al. | 600/457 |
| 5,108,411 A | 4/1992 | McKenzie | |
| 5,201,316 A | 4/1993 | Pomeranz et al. | |
| 5,503,155 A * | 4/1996 | Salmon et al. | 600/463 |
| 5,596,991 A * | 1/1997 | Tanaka | 600/459 |
| 5,715,816 A * | 2/1998 | Mainiero et al. | 600/323 |
| 6,142,945 A * | 11/2000 | Sakamoto et al. | 600/459 |
| 6,210,363 B1 * | 4/2001 | Esch et al. | 604/96.01 |
| 6,261,246 B1 | 7/2001 | Pantages et al. | |
| 6,645,149 B1 | 11/2003 | Smith | |
| 2002/0026128 A1 | 2/2002 | White et al. | |
| 2005/0261582 A1 | 11/2005 | Becker et al. | |
| 2006/0100492 A1 * | 5/2006 | Hartle et al. | 600/350 |
| 2006/0278248 A1 * | 12/2006 | Viswanathan | 128/899 |

FOREIGN PATENT DOCUMENTS

WO      WO 00/61005       10/2000

OTHER PUBLICATIONS

Urbanowicz et al., Transesophageal Echocardiography and its Potential for Esophageal Damage, Jan. 1990, Anesthesiology, V 72, No. 1, p. 40-43.*

* cited by examiner

*Primary Examiner* — Jacqueline Cheng
(74) *Attorney, Agent, or Firm* — Day Pitney LLP (57) ABSTRACT

An oesophageal Doppler monitoring probe is comprised of an elongated flexible shaft having a distal end and a proximal end. In one embodiment, the elongated flexible shaft includes a pitched spring. The probe further includes a probe tip coupled to the distal end, wherein the probe tip includes an ultrasound transducer assembly, and a connector coupled to the proximal end, wherein the connector is configured to electrically couple the monitoring probe to a host processor. In one embodiment, the ultrasound transducer assembly may be configured to detect blood flow characteristics based on the Doppler effect.

23 Claims, 5 Drawing Sheets

Fig. 4B

FLEXIBLE OESOPHAGEAL DOPPLER MONITORING PROBE

FIELD OF THE INVENTION

The present invention relates in general to ultrasound probes and, in particular, to a flexible oesophageal Doppler monitoring probe.

BACKGROUND

A transoesophageal echocardiogram, or TOE (TEE in the United States) utilizes a special probe containing an ultrasound transducer in its tip, which is passed into the patient's oesophagus. This procedure is considered to be superior to the more traditional non-invasive transthoracic echocardiogram since it is able to produce clearer images, especially of structures that are otherwise difficult to view transthoracicly. Since the heart rests directly upon the oesophagus leaving only millimeters in distance that the ultrasound beam has to travel, there is little attenuation of the ultrasound signal, thereby generating a stronger return signal. This results in an enhanced image and improved ultrasound quality.

It is generally recognized that several pulmonary structures can be evaluated and imaged with TOE, including the aorta, pulmonary artery, valves of the heart, both atria, atrial septum, left atrial appendage, as well as the coronary arteries. Recently, however, the principles underlying TOE have been expanded and improved upon. In particular, oesophageal Doppler monitoring has been developed and used to combat the condition known as hypovolaemia, which is a pronounced reduction in circulating blood volume. Hypovolaemia may result from the combined effects of pre-operative fasting, the anaesthetic agent and blood loss during the surgical procedure. The complications that hypovolaemia causes arise because the reduced circulating blood volume is unable to carry sufficient oxygen to the major organs and tissues. Patients undergoing surgery are constantly at risk from this serious and potentially life-threatening condition.

Oesophageal Doppler monitoring is premised on the Doppler effect, which in the broadest sense is the change in frequency and wavelength of a wave as perceived by an observer moving relative to the source of the waves. In the context of the cardiovascular system, the Doppler effect can be used to measure the speed and direction of blood flow leaving the heart. This information may then be used to detect any reduction in circulating blood volume early and in real-time. This allows the anesthetist to intervene quickly and safely to correct the situation, using a combination of specialized fluids and drugs, before the hypovolaemia becomes more serious.

Figure 1A:
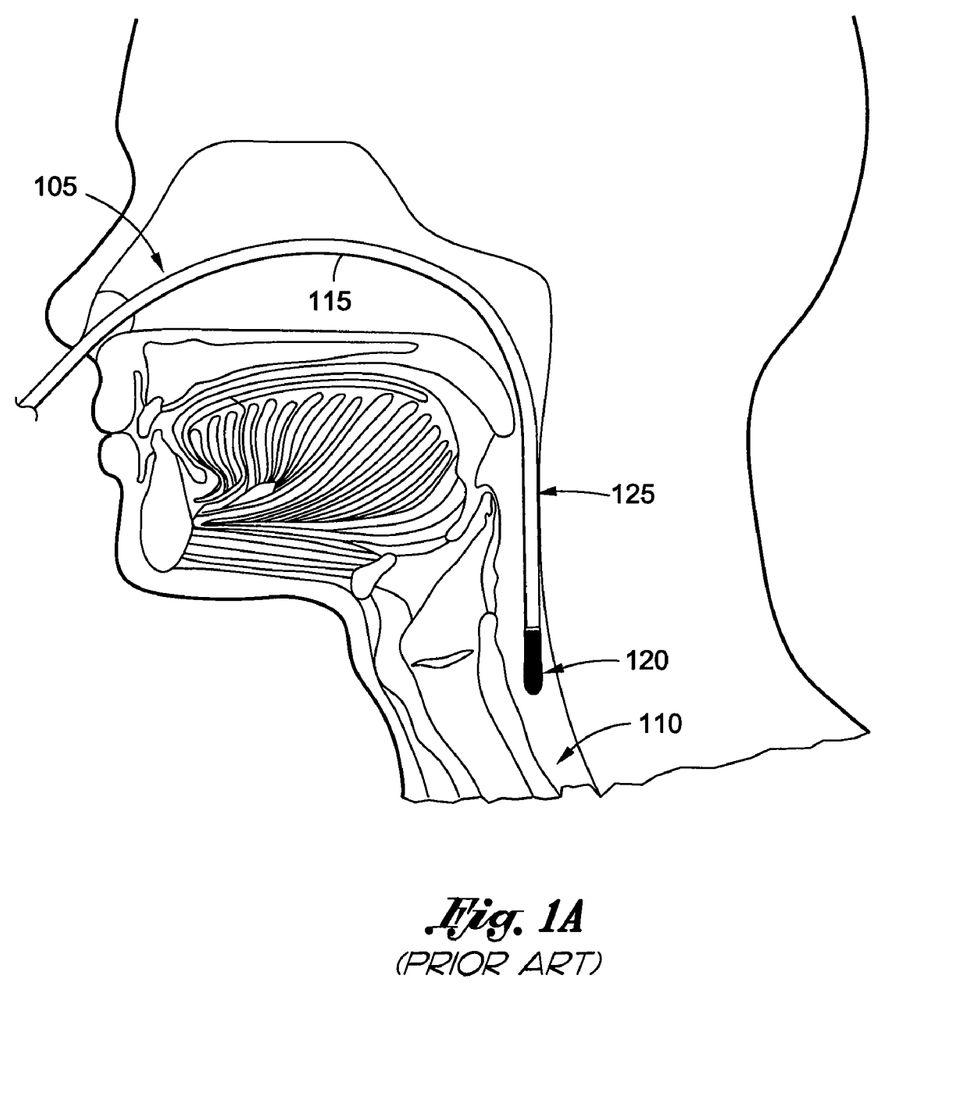
FIG. 1A is a cross-sectional view of a patient following the insertion of a prior art oesophageal monitoring probe.

The insertion of prior art Doppler probes for TOE and oesophageal Doppler monitoring procedures is unfortunately very uncomfortable to the awake patient. As shown in FIG. 1A, the Doppler probe 120 is attached to the end of a shaft 115, which is being used to manually advance the probe tip 120 into and through the patient's nasal cavity 105, past the pharynx, into the oesophagus 110 itself, and ultimately to a level of between the $5^{th}$ and $6^{th}$ thoracic ribs (referred to as the "T5 to T6 level"). It should be noted that the probe tip 120 of FIG. 1A is depicted in an intermediate or transition state during insertion, but prior to reaching its focused position at the T5 to T6 level.

Proper placement and orientation of the probe tip 120 is critical to the monitoring process. As such, in order to be able to properly manipulate the position and orientation of the probe tip 120 once inserted, the prior art shaft 115 is made to be resiliently bendable. This resiliency or rigidity is imparted using a tightly wound spring which traverses the length of the shaft 115.

Figure 1B:
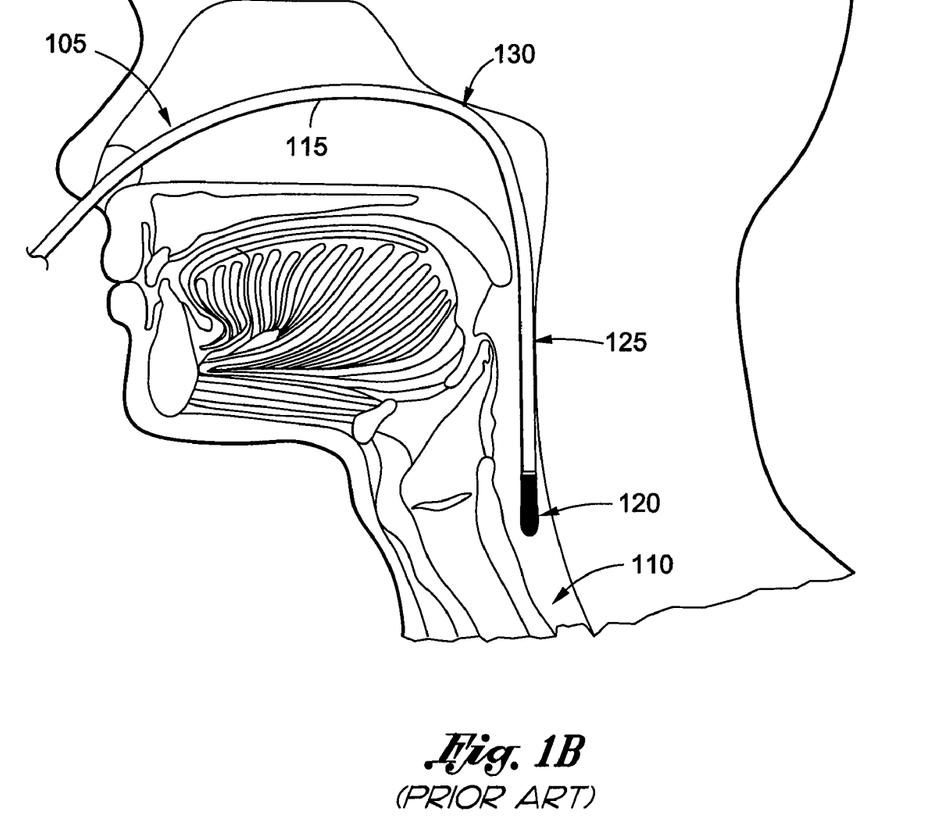
FIG. 1B is another cross-sectional view of a patient following the insertion of a prior art oesophageal monitoring probe.

In addition to the rigidity and resulting abrasiveness of the probe tip 120 itself, the resilient nature of the prior art shaft 115 tends to exert a constant and sizable force against the wall of the oesophagus in the general vicinity of area 125. For example, the typical prior art shaft (e.g., shaft 115) would exert a force on the order of 120 gram-force (gf) against the oesophagus wall. FIG. 1B shows that, in addition to the discomfort experienced by patients along the walls of the oesophagus (i.e., area 125), the top of the nasal cavity 130 will also tend to be a source of discomfort since the inwardly-directed pressure is concentrated around this area, and essentially used to force the shaft downward through the pharynx and into the oesophageal area.

Exacerbating the discomfort associated with Doppler probe insertions is that, unlike traditional TOE procedures, oesophageal Doppler monitoring at times cannot be performed while the patient is sedated. For example, it has been found that oesophageal Doppler monitoring can be beneficial during awake-patient surgery and during post-operative recovery periods. Not only does the awake state dramatically increase the physical discomfort associated with the oesophageal Doppler monitoring procedure, the patient's gag reflex may also complicate successful completion of the procedure itself.

Thus, there is a need in the art for an improved oesophageal Doppler monitoring probe and system which reduces the discomfort associated with probe insertion.

BRIEF SUMMARY OF THE INVENTION

Disclosed and claimed herein are oesophageal Doppler monitoring probes and probe shafts. In one embodiment, an oesophageal Doppler monitoring probe includes an elongated flexible shaft having a distal end and a proximal end, wherein the elongated flexible shaft comprises a pitched spring extending through the elongated flexible shaft and configured to impart a flexural stiffness of between 0.00025 and 0.0005 $Nm^2$. The probe tip is coupled to the distal end and includes an ultrasound transducer assembly. A connector is coupled to the proximal end and is configured to electrically couple the monitoring probe to a host processor.

Other aspects, features, and techniques of the invention will be apparent to one skilled in the relevant art in view of the following detailed description of the invention.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION OF EXEMPLARY EMBODIMENTS

Disclosure Overview

One aspect of the present disclosure relates to an elongated flexible shaft for use with an oesophageal Doppler monitoring probe. As will be described in more detail below, the shaft includes a pitched spring extending through a length of the sheath, where the pitched spring is configured to impart a flexural stiffness of between 0.00025 and 0.0005 $Nm^2$. The distal end of the shaft is configured to be coupled to a probe tip having an ultrasound transducer, while the proximal end is configured to be coupled to a host processor connector.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner on one or more embodiments without limitation.

Exemplary Embodiments

Figure 2:
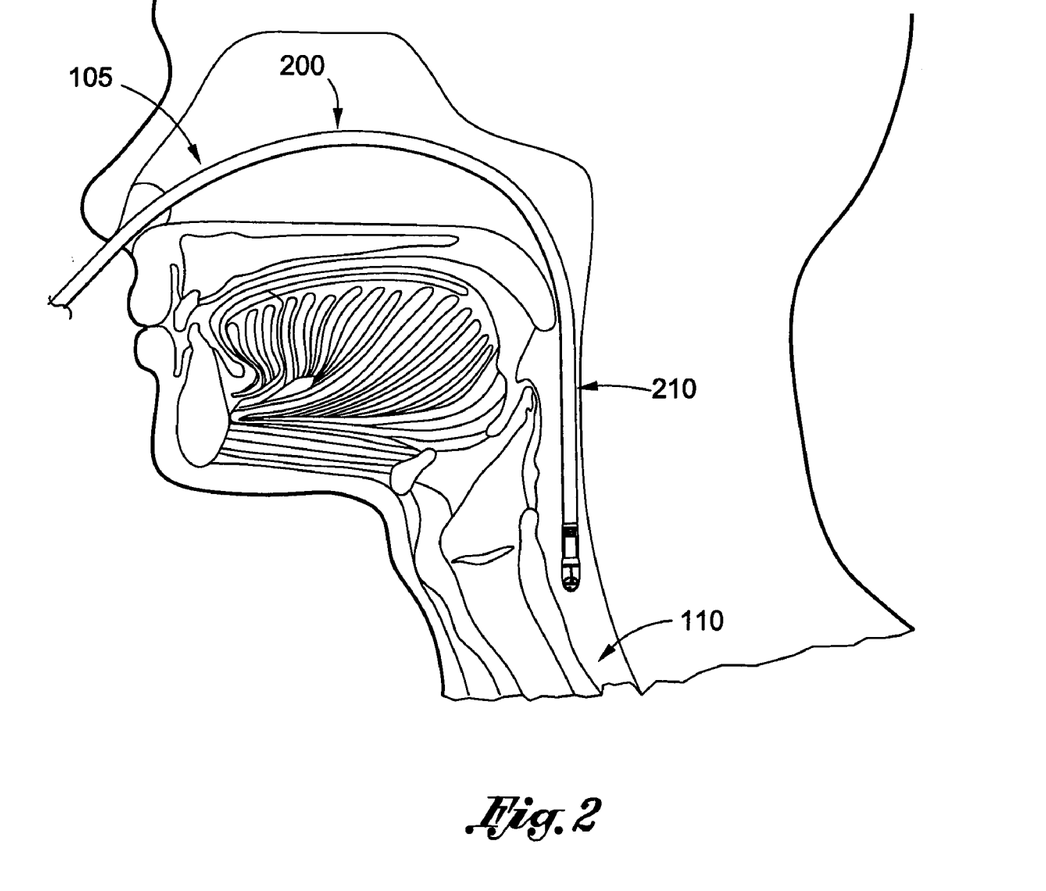
FIG. 2 is a cross-sectional view of a patient following the insertion of one embodiment of a flexible oesophageal monitoring probe configured in accordance with the principles of the invention.

Referring now to FIG. 2, depicted is one embodiment of a flexible oesophageal Doppler monitoring probe 200, configured in accordance with the principles of the invention. While in one embodiment the probe 200 may be a disposable oesophageal Doppler monitoring probe having a predetermined lifespan, it should equally be appreciated that the probe 200 may alternatively be durable and reusable.

As shown, the probe 200 is being inserted into a patient's nasal cavity 105 and then down into the patient's oesophagus 140. For comparison to the prior art probes of FIGS. 1A-1B, the probe 200 is depicted in FIG. 2 as being in a similar intermediate or transition state prior to reaching its focused position at the T5 to T6 level.

However, unlike the oesophageal probes of the prior art (e.g., probe 120), the probe 200 is sufficiently flexible that it does not cause the level of irritation and discomfort that prior art probes do. In one embodiment, the probe 200 may be configured to apply minimal or no force against the nasal cavity, as is many times the case with prior art probes (see FIG. 1B). In addition, the probe 200 may be sufficiently compliant so as to impart only a minimal force against the wall of the oesophagus in the general vicinity of area 210. To that end, the probe 200 may exert a force on the order of only 25 gf against the oesophagus wall in contrast to the approximate 120 gf of prior art probes (e.g., probe 120).

Figure 3A:
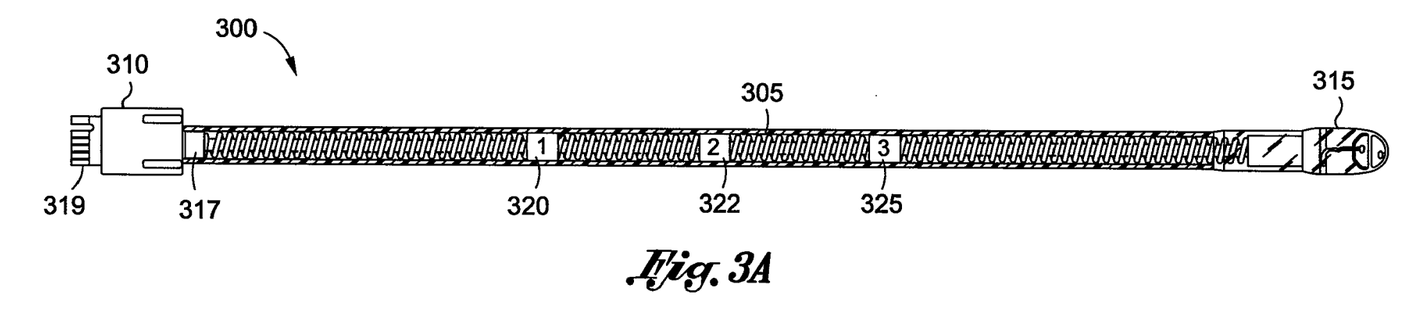
FIGS. 3A-3C depict cross-sectional views of various parts of the flexible oesophageal monitoring probe of FIG. 2.

Referring now to FIG. 3A, depicted is partial cross-sectional of one embodiment of the flexible oesophageal Doppler monitoring probe 200 of FIG. 2. In this embodiment, the probe 300, which may be a disposable probe having a predefined lifespan, is comprised of an elongated flexible shaft 305 having a connector 310 coupled to a proximal end and a probe tip 315 coupled to a distal end, as shown in FIG. 2.

It should be appreciated that it may be desirable to couple the probe 300 to a host processor (not shown) in order to record and analyze patient-specific physiological information, such as the onset of hypovolaemia. To that end, the connector 310 may be used to electrically couple the probe 300 to such a host system. By way of a non-limiting example, one embodiment of the connector 310 may be as disclosed in U.S. Pat. No. 6,645,149, the contents of which are fully hereby incorporated by reference.

The connector 310 may further include an electronic memory configured to receive and store probe and/or patient use parameters. Additionally, such memory may include a parameter used by the host system to detect when the usable life of the probe 300 expires. The memory may also contain patient-specific data and the like.

In one embodiment, the connector 310 may be electrically connected to the host system via one or more printed circuit board connectors 319, although obviously other types of electrical connectors may similarly be used. The connector 310 may further include a identification band 317, usable to provide identifying information to a user of the probe 300, for example.

The elongated flexible shaft 305 of FIG. 3A is shown in cross-sectional form. As will be described in more detail below with reference to FIGS. 3B-3C, the shaft 305 includes a pitched spring that, in one embodiment, extends from the connector 310 to the probe tip 315. The shaft 305 also is depicted as including a first depth marker 320, a second depth marker 322 and a third depth marker 325. In one embodiment, the depth markers 320, 322 and 325 may be usable to determine when the proper probe depth has been reached based, for example, on patient age, height, etc. By way of illustration, when inserted into the nasal cavity (e.g., nasal cavity 105), the user may continue to insert the probe 300 until the appropriate marker (e.g., marker 320, 322 or 325) for the given patient reaches a predetermined point, such as the entrance of the nasal cavity. While three depth markers have been depicted in FIG. 3A, it should equally be appreciated that additional or fewer markers may be oriented along the length of the shaft 305 corresponding to different patient ages, heights, or any other physical characteristic.

Figure 3B:
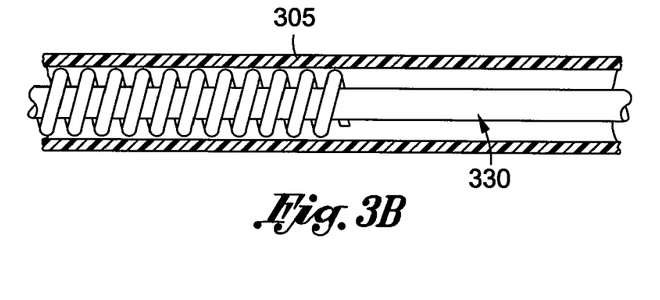

Referring now to FIG. 3B, depicted is another cross-sectional view of the elongated flexible shaft 305 depicting how, in one embodiment, an electrical wire or cable 330 extends through the center of the shaft 305 encircled or otherwise surrounded by a pitched spring 335. In one embodiment, the cable 330 may be configured to carry electrical signals between an ultrasound transducer in the probe tip 315 (see FIGS. 4A-4B) and the connector 310. In certain embodiments, it may be desirable for the cable 330 to be highly flexible, so as not to otherwise impact the overall flexural stiffness of the shaft 305.

Figure 3C:
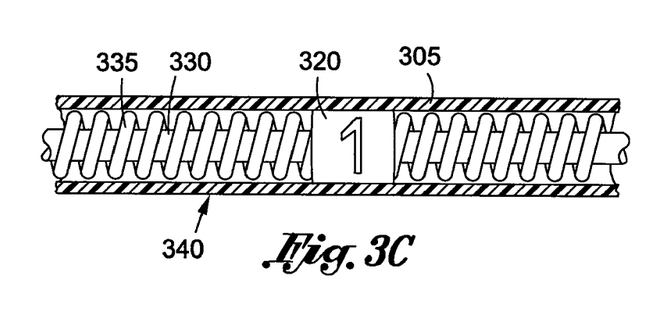

With reference now to FIG. 3C, depicted is still another cross-sectional view of an elongated flexible shaft 305 configured in accordance with the principles of the invention. In this embodiment, a close up view is provided of the elongated flexible shaft 305 and the depth marker 320. Additionally, the external sheath 340 of the shaft 305 may be comprised of a tube-shape material, such as a silicone-based tubing. While in one embodiment, the sheath 340 may be a clear material, in other embodiments it may be opaque, translucent or have a solid color.

Continuing to refer to the shaft 305 of FIGS. 3A-3C, in one embodiment the elongated flexible shaft 305 may be characterized by a flexural stiffness of between 0.00025 and 0.0005 Nm², where the term "flexural stiffness" is a measure of the resistance of a structure to bending (Roark, R. J. *Formulas for Stress and Strain*, 1943, 2nd ed., McGraw-Hill, New York). In one embodiment, the flexural stiffness of the shaft may be calculated according to (1) below:

$$\text{Flexural stiffness} = \frac{FL^3}{3y}, \quad (1)$$

where F is the force applied to the shaft, L is the length of the shaft, and y is the deflection at the free end of the shaft.

While other lengths may be used consistently with the principles of the invention, the elongated flexible shaft 305 has a length of between 800 and 900 millimeters and a diameter of between 5 and 7 millimeters.

With respect to the depicted pitched spring 335, a total of between 360 and 460 coils may be used. Alternatively, the number of coils of the pitched spring 335 may be represented on a 'per unit' basis and be between 6 and 9 coils per centimeter. Additionally, the wire diameter for the pitched spring 335 may be between 0.6 and 0.9 millimeters, although other thickness may be used in accordance with the principles of the invention.

In accordance with the principles of the invention, the aforementioned spring configuration may enable the elongated flexible shaft 305 to provide a torsional stiffness of between 0.0003 and 0.0012 Nm². In one embodiment, the flexural stiffness of the shaft may be calculated according to (2) below:

$$\text{Torsional stiffness} = \frac{Fd}{\theta/L}, \quad (2)$$

where F is the force applied at a moment arm d, L is the length of the shaft, and the θ is the resulting rotation in radians.

Thus, in contrast to the oesophageal probes of the prior art (e.g., probe 120), the elongated flexible shaft 305 of the present disclosure may exhibit a combination of flexibility (e.g., flexural stiffness of between 0.00025 and 0.0005 Nm²) and high torsional stiffness (e.g., torsional stiffness of between 0.0003 and 0.0012 Nm²), thereby permitting substantially reduced levels of irritation and discomfort associated with the probe insertion procedure, while still providing the user with full control over probe positioning and orientation. In one embodiment, this may be accomplished using one embodiment of the pitched spring 335 having between 6 and 9 coils per centimeter. Based thereon, oesophageal Doppler monitoring, such as the monitoring used for detecting hypovolaemia, may be performed on awake patients with only minor discomfort.

Figure 4A:
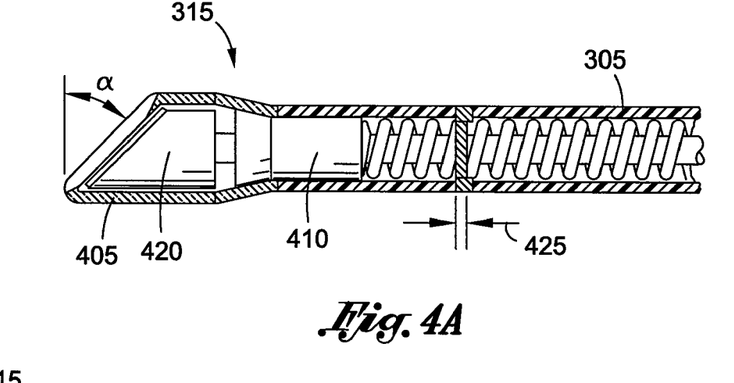
FIG. 4A depicts a cross-sectional view of a probe tip configured in accordance with one embodiment of the invention.

While the spring 335 has been heretofore described as being pitched, it should be appreciated that in one embodiment its entire length may be pitched, while in another embodiment only that portion of the spring which enters the body need be pitched. Thus, the spring corresponding to the portion of the elongated flexible shaft 305 which remains outside of the body may be of the closed coil variety. Put another way, the pitched spring 335 may comprise both a pitched portion and a closed portion. The pitched portion may correspond to a part or length of the elongated flexible shaft that enters the human body, while the closed portion may correspond to the part of the elongated flexible shaft would not be entering the human body FIG. 4A depicts an enlarged cross-sectional view of the probe tip 315 of the oesophageal Doppler monitoring probe 300 of FIGS. 3A-3C. Specifically, the probe tip 315 comprises a boot 405 that encapsulates an insulating sleeve 410 and a Doppler or ultrasound transducer assembly 420. The boot 405 is adhesively coupled to the shaft 305 along adhesive interface 425.

In one embodiment, the insulating sleeve 410 may serve to insulate or otherwise isolate the ultrasound transducer assembly 420 from the pitched spring 335 and mechanical forces being transferred through the length of the shaft 305 during the insertion and positioning operations. The insulating sleeve 410 may also function to contain and insulate the cable 330, as well as to provide a degree of flexibility in the probe tip 315 itself.

As depicted in FIG. 4A, the end of the probe tip 315 may be oriented at an angle α of between 30 degrees and 60 degrees offset from the plane essentially perpendicular to the elongated flexible shaft 305. In one embodiment, this angle may be approximately 45 degrees (±5 degrees).

With respect to the transducer assembly 420, in one embodiment it may comprise a Doppler transducer assembly configured to detect a speed of blood flow based on the Doppler effect. In certain embodiments, the ultrasound transducer assembly 420 may comprise a piezoelectric transducer that convert electrical energy into sound. As is known in the art of piezoelectric crystals, such crystals have the property of changing size when a voltage is applied. Thus, the application of an alternating voltage across them will cause the crystals to oscillate at very high frequencies, thus producing very high frequency sound waves. Such sound waves may then be used, in combination with the principles of the Doppler effect, to determine various blood flow characteristics.

Figure 4B:
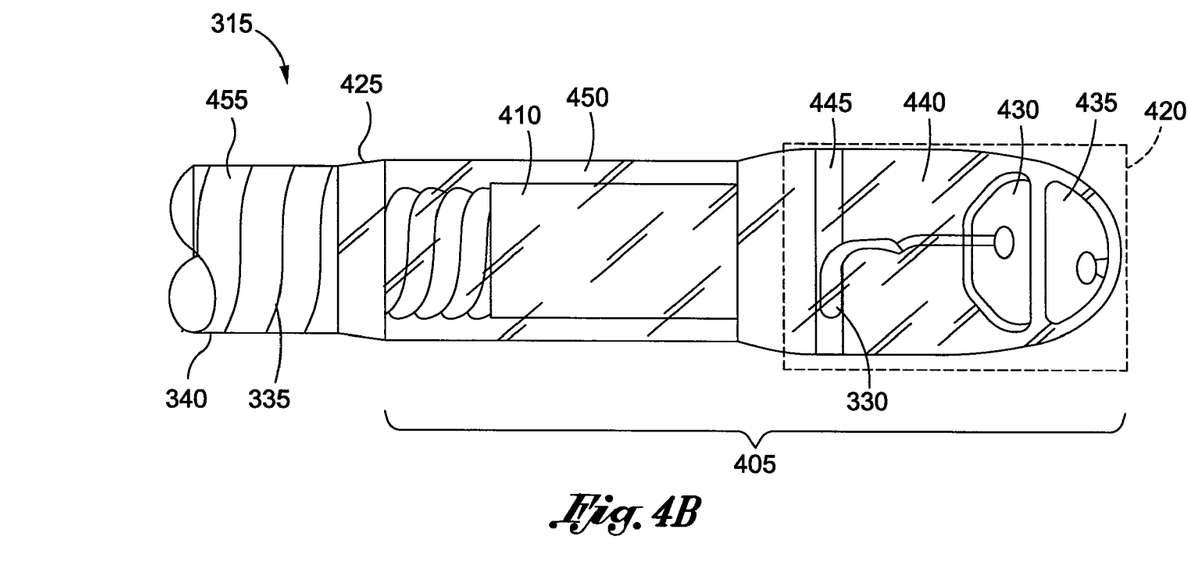
FIG. 4B illustrates a probe tip configured in accordance with another embodiment of the invention.

Referring now to FIG. 4B, depicted is an enlarged side view of the probe tip 315 of the oesophageal Doppler monitoring probe 300. Beginning on the left side of FIG. 4B, the spring 335 is shown as being in contact with the adhesive interface 425. The portion of the sheath 340, which is itself see-through, surrounding the spring 335 in FIG. 4B has been filled with an opaque or otherwise non-see-through material 455, such as a white silicone-based sealant or adhesive material. However, it should equally be appreciated that the material surrounding the spring 335 may be similarly clear. Regardless, one function of material 455 may be to secure the position of the spring 335 and cable 330 within the sheath 340, while not materially altering the flexural and torsional stiffness properties of the spring 335.

Continuing to refer to FIG. 4B, unlike prior art probes, the boot 405 may be manufactured to be see-through (e.g., clear or translucent) such that the components it encapsulates are readily visible. Moreover, the boot 405 may be filled with a clear or translucent material 450, such as a clear-silicone based sealant or adhesive material. In this fashion, the components within the boot 405 may remain visible, yet the clear/translucent material 450 may still function to secure in place the various components within the boot 450. While the clear/translucent material 450 is shown surrounding the sleeve 410, it should also be appreciated that the material 450 may also surround and secure the components comprising the ultrasound transducer assembly 420.

As with the embodiment of FIG. 4A, the end of the probe tip 315 of FIG. 4B may be similarly oriented at an angle (not shown) of between 30 degrees and 60 degrees offset from the plane essentially perpendicular to the elongated flexible shaft 305. In one embodiment, this angle may be approximately 45 degrees (±5 degrees). In order to accommodate this angled design, the clear/translucent material 450 comprising the end of the boot 405 may be molded at the requisite angle.

Additionally, in the embodiment of FIG. 4B the depicted ultrasound transducer assembly 420 is a piezoelectric crystal transducer, as described above. The transducer assembly 420 includes a first piezoelectric crystal 430 and a second piezoelectric crystal 435. These crystals 430 and 435 and mounted on a molded substrate 440, which in one embodiment may be comprised of acrylonitrile butadiene styrene (ABS) plastic. The cable 330, which is situated in a recess 445 of the 450 so as to minimize the overall width of the transducer assembly 420, is configured to provide electrical signals to and from the crystals 430 and 435. It should be appreciated that other ultrasound transducer configurations may similarly be used consistently with the principles of the invention.

In certain embodiments, the see-through boot 405 may be substantially biocompatible since there is no or little pigment in the material. Moreover, a see-through boot 405, in combination with the clear/translucent material 450, facilitates the visual inspection of the internal components both during and after the manufacturing process. By way of example, the clear/translucent material 450 may be a resin-type material which requires that a curing process be performed. To that end, when a clear or otherwise see-through boot is used (e.g., see-through boot 405), ultraviolet light may be used to cure the material, thereby substantially decreasing the time required to manufacture the probe tip 315, as well as improving the accuracy of the process since the boot 405 will already be secured in place over the ultrasound transducer assembly 420. In this fashion, the cost associated with the manufacturing process of the probe tip 315 may be reduced.

Additionally, quality control may be significantly increased due to the fact that defective units may be readily identified by mere visual inspection. For example, providing visual inspection of the sealant during the manufacturing process may improve the ability to detect and prevent air bubbles in the sealant. Such air bubbles tend to reflect and scatter ultrasound and, therefore, reduce efficiency of ultrasound emission and reception.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Trademarks and copyrights referred to herein are the property of their respective owners.

What is claimed is:

1. An oesophageal Doppler monitoring probe comprising:
   an elongated flexible shaft having a distal end and a proximal end, wherein the elongated flexible shaft comprises a single pitched spring extending through the elongated flexible shaft and configured to impart a flexural stiffness of between 0.00025 and 0.0005 $Nm^2$, wherein the elongated flexible shaft has a diameter of between 5 and 7 millimeters;
   a probe tip coupled to the distal end, wherein the probe tip includes an ultrasound transducer assembly;
   a connector coupled to the proximal end, wherein the connector is configured to electrically couple the monitoring probe to a host processor; and
   an electrical cable disposed within the single pitched spring to electrically connect the ultrasound transducer assembly at the distal end to the connector at the proximal end.

2. The oesophageal Doppler monitoring probe of claim 1, wherein the ultrasound transducer assembly is configured to detect a speed of blood flow based on a Doppler effect.

3. The oesophageal Doppler monitoring probe of claim 1, wherein the pitched spring has between 6 and 9 coils per centimeter.

4. The oesophageal Doppler monitoring probe of claim 1, wherein the pitched spring has a total of between 360 and 460 coils.

5. The oesophageal Doppler monitoring probe of claim 1, wherein the elongated flexible shaft has a torsional stiffness of between 0.0003 and 0.0012 $Nm^2$.

6. The oesophageal Doppler monitoring probe of claim 1, wherein the pitched spring has a wire diameter of between 0.6 and 0.9 millimeters.

7. The oesophageal Doppler monitoring probe of claim 1, wherein the elongated flexible shaft has a length of between 800 and 900 millimeters.

8. The oesophageal Doppler monitoring probe of claim 1, wherein the elongated flexible shaft further includes one or more depth markers situated at corresponding one or more predetermined positions.

9. The oesophageal Doppler monitoring probe of claim 1, wherein the probe tip is oriented at an angle of between 40 degrees and 50 degrees offset from a plane essentially perpendicular to the elongated flexible shaft.

10. The oesophageal Doppler monitoring probe of claim 1, wherein said angle is approximately 45 degrees.

11. The oesophageal Doppler monitoring probe of claim 1, wherein the pitched spring has a pitched portion and a closed portion, wherein the pitched portion corresponds to a first length of the elongated flexible shaft that enters a human body, and the closed portion corresponds to a second length of the elongated flexible shaft that does not enter the human body.

12. The oesophageal Doppler monitoring probe of claim 1, wherein the probe tip comprises a see-through boot.

13. The oesophageal Doppler monitoring probe of claim 1, wherein the elongated flexible shaft is configured to exert no more than about 25 gram-force against an oesophagus wall when inserted into an oesophagus.

14. An elongated flexible shaft for use with an oesophageal Doppler monitoring probe, the shaft comprising:
   a sheath;
   a single pitched spring extending through a length of the sheath, the pitched spring configured to impart a flexural stiffness of between 0.00025 and 0.0005 $Nm^2$, wherein the elongated flexible shaft has a diameter of between 5 and 7 millimeters;
   a distal end configured to be coupled to a probe tip having an ultrasound transducer assembly;
   a proximal end configured to be coupled to a host processor connector; and
   an electrical cable disposed within the single pitched spring to electrically connect the ultrasound transducer assembly at the distal end to the host processor connector at the proximal end.

15. The elongated flexible shaft of claim 14, wherein the ultrasound transducer assembly is configured to detect a speed of blood flow based on a Doppler effect.

16. The elongated flexible shaft of claim 14, wherein the pitched spring has between 6 and 9 coils per centimeter.

17. The elongated flexible shaft of claim 14, wherein the pitched spring has a total of between 360 and 460 coils.

18. The elongated flexible shaft of claim 14, wherein the elongated flexible shaft is characterized by a torsional stiffness of between 0.0003 and 0.0012 $Nm^2$.

19. The elongated flexible shaft of claim 14, wherein the pitched spring has a wire diameter of between 0.6 and 0.9 millimeters.

20. The elongated flexible shaft of claim 14, wherein the elongated flexible shaft has a length of between 800 and 900 millimeters.

21. The elongated flexible shaft of claim 14, further comprising one or more depth markers situated at corresponding one or more predetermined positions.

22. The elongated flexible shaft of claim 14, wherein the pitched spring has a pitched portion and a closed portion, wherein the pitched portion corresponds to a first length of the elongated flexible shaft that enters a human body, and the closed portion corresponds to a second length of the elongated flexible shaft that does not enter the human body.

23. The elongated flexible shaft of claim 14, wherein the elongated flexible shaft is configured to exert no more than about 25 gram-force against an oesophagus wall when inserted into an oesophagus.

* * * * *